(12) United States Patent
Sprague et al.

(10) Patent No.: US 9,387,214 B2
(45) Date of Patent: Jul. 12, 2016

(54) METHOD OF IDENTIFYING THERAPIES FOR PULMONARY HYPERTENSION

(71) Applicant: United Therapeutics Corporation, Silver Spring, MD (US)

(72) Inventors: Randy Stephen Sprague, Webster Groves, MO (US); Alan Howard Stephenson, Manchester, MO (US); Mary Litchfield Ellsworth, Manchester, MO (US); Elizabeth A. Bowles, St. Louis, MO (US)

(73) Assignee: United Therapeutics Corporation, Silver Spring, MD (US)

( * ) Notice: Subject to any disclaimer, the term of this patent is extended or adjusted under 35 U.S.C. 154(b) by 26 days.

(21) Appl. No.: 13/738,232

(22) Filed: Jan. 10, 2013

(65) Prior Publication Data

US 2013/0184295 A1 Jul. 18, 2013

Related U.S. Application Data

(60) Provisional application No. 61/586,452, filed on Jan. 13, 2012.

(51) Int. Cl.

| | | |
|---|---|---|
| *A61K 31/5575* | (2006.01) | |
| *A61K 31/519* | (2006.01) | |
| *A61K 31/4985* | (2006.01) | |
| *A61P 11/00* | (2006.01) | |
| *C12Q 1/02* | (2006.01) | |
| *G01N 33/50* | (2006.01) | |

(52) U.S. Cl.
CPC .......... *A61K 31/5575* (2013.01); *A61K 31/519* (2013.01); *C12Q 1/025* (2013.01); *G01N 33/5044* (2013.01); *G01N 2800/321* (2013.01)

(58) Field of Classification Search
CPC ............ A61K 31/5575; A61K 31/519; A61K 31/4985
USPC ........... 514/573, 569, 261.1, 254.09; 562/466
See application file for complete search history.

(56) References Cited

U.S. PATENT DOCUMENTS

| | | |
|---|---|---|
| 5,153,222 A | 10/1992 | Tadepalli et al. |
| 6,521,212 B1 | 2/2003 | Cloutier et al. |
| 6,756,033 B2 | 6/2004 | Cloutier et al. |
| 7,384,978 B2 | 6/2008 | Phares et al. |
| 7,417,070 B2 | 8/2008 | Phares et al. |
| 7,544,713 B2 | 6/2009 | Phares et al. |
| 8,232,316 B2 | 7/2012 | Phares et al. |
| 8,252,839 B2 | 8/2012 | Phares et al. |
| 8,410,169 B2 | 4/2013 | Phares et al. |
| 8,536,363 B2 | 9/2013 | Phares et al. |
| 8,609,728 B2 | 12/2013 | Rothblatt et al. |
| 2007/0078095 A1 | 4/2007 | Phares et al. |
| 2008/0200449 A1 | 8/2008 | Olschewski et al. |
| 2010/0076083 A1 | 3/2010 | Olschewski et al. |
| 2012/0216801 A1 | 8/2012 | Olschewski et al. |
| 2013/0253049 A1 | 9/2013 | Rothblatt et al. |
| 2013/0261187 A1 | 10/2013 | Phares et al. |

OTHER PUBLICATIONS

McLaughlin et al. Journal of the American College of Cardiology 2010, 55 (18), 1915-1922.*
Adderley et al. Med. Sci. Monit. 2011, 17 (5), CR241-247.*
Adderley et al. Am. J. Physiol. Heart Circ. Physiol. 2009, 296, H1617-1624.*
Chou Cancer Res. 2010, 70 (2), 440-446.*

\* cited by examiner

*Primary Examiner* — Sreeni Padmanabhan
*Assistant Examiner* — Irina Neagu
(74) *Attorney, Agent, or Firm* — Foley & Lardner LLP

(57) ABSTRACT

The present invention is directed to a method of screening for a therapeutic agent useful for treating pulmonary hypertension comprising: contacting an erythrocyte with a candidate therapeutic agent; and detecting a presence or absence of erythrocyte-derived adenosine triphosphate, wherein a greater erythrocyte-derived adenosine triphosphate level indicates the candidate therapeutic agent has greater activity in treating pulmonary hypertension. Additionally, the present invention is directed to methods of treating pulmonary arterial hypertension by stimulating ATP release from erythrocytes through co-administration to a subject in need thereof an amount of a PDE5 inhibitor compound, and an amount of a prostacyclin compound.

7 Claims, 3 Drawing Sheets

Figure 1. Identification of the PDE5A isoform in human erythrocytes
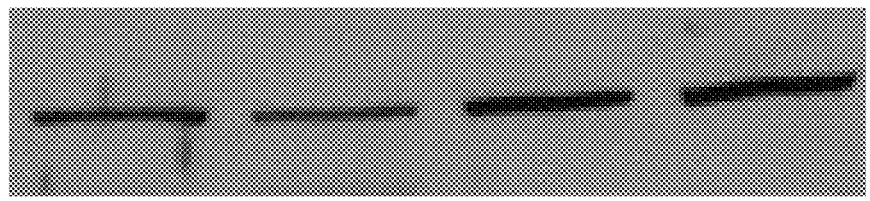

Figure 2. Effect of Zaprinast on UT-15C Induced ATP Release From Healthy Human Erythrocites
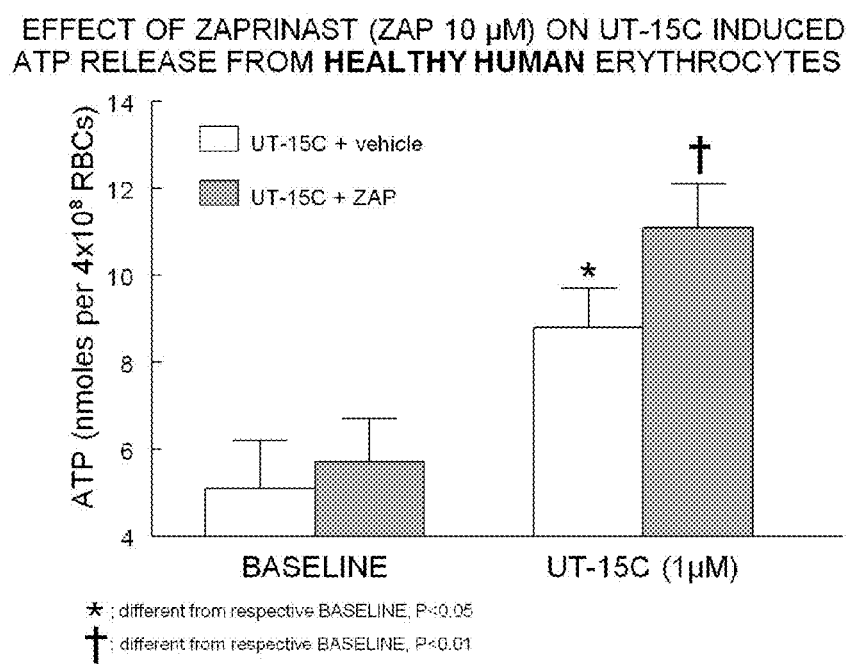

Figure 3. Further Effect of Zaprinast on UT-15C Induced ATP Release From Healthy Human Erythrocites
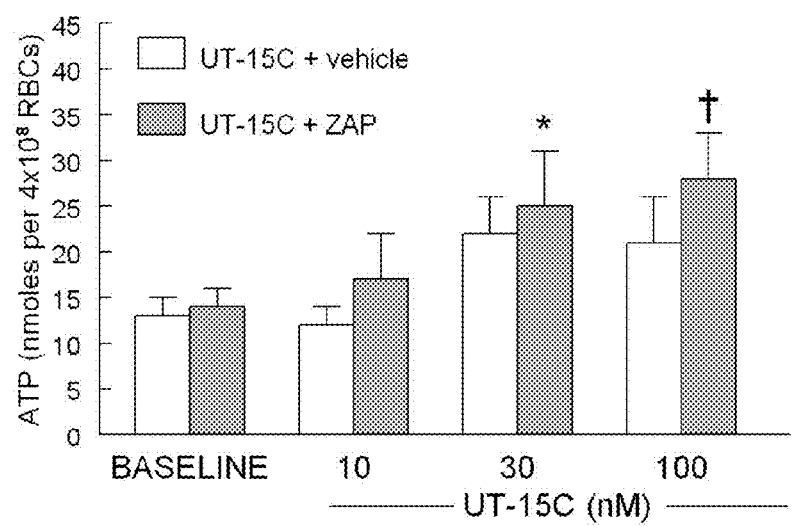

METHOD OF IDENTIFYING THERAPIES FOR PULMONARY HYPERTENSION

CROSS-REFERENCE TO RELATED APPLICATIONS

This application claims priority from U.S. Provisional Application 61/586,452, filed Jan. 13, 2012. The entire contents of the aforementioned application is incorporated herein by reference.

BACKGROUND OF THE INVENTION

Pulmonary arterial hypertension (PAH) is a progressive lung disorder which, untreated, leads to death on average within 2.8 years after being diagnosed. An increasing constriction of the pulmonary circulation leads to increased stress on the right heart, which may develop into right heart failure. PAH is a disease of uncertain etiology that leads to right ventricular failure, and ultimately death.

Although many causes and conditions are found to be associated with PAH, many of them share in common several fundamental pathophysiological features. One important feature among these processes is dysfunction of the endothelium, the internal cellular layer of all vessel walls, which is normally responsible for the production and metabolism of a large array of substances that regulate vessel tone and repair and inhibit clot formation. In the setting of PAH, endothelial dysfunction can lead to excessive production of deleterious substances and impaired production of protective substances. Whether this is the primary event in the development of PAH or part of a downstream cascade remains unknown, but in either case it is an important factor in the progressive vasoconstriction and vascular proliferation that characterize the disease.

Abnormalities in three major endothelium-based pathways have been identified that serve as the basis for current treatments for PAH:

(1) Overproduction of endothelin. Endothelin is a vasoconstrictor and angiogenic substance that is produced in excess by the injured endothelium in PAH. By blocking the receptor, endothelin-receptor antagonists (ERAs) neutralize the consequences of excessive endothelin synthesis and produce clinical benefit.

(2) Underproduction of Nitric Oxide (NO). Nitric oxide is a potent vasodilator and inhibitor of vascular proliferation that is under produced by the injured pulmonary vascular endothelium in PAH. Nitric oxide mediates these effects through cyclic GMP. By inhibiting the breakdown of the enzyme that catabolizes cGMP, phosphodiesterase type-5 inhibitors (PDE5) such as sildenafil and tadalafil augment cGMP, thereby minimizing the impact of diminished NO activity in PAH, with resulting clinical benefit.

(3) Underproduction of prostacyclin. Prostaglandins are a heterogeneous family of endoperoxides that are produced in a variety of organ systems and cells and have a number of important regulatory activities. In the vasculature, prostaglandin 12 ($PGI_2$, prostacyclin) is the most abundant and important prostacyclin produced by the endothelium, and serves as a potent vasodilator and inhibitor of growth and proliferation. As with NO, prostacyclin production by the pulmonary vascular endothelium is diminished in the setting of PAH. Treatment of PAH with prostacyclin or an agonist thereof has resulted in clinical benefit in PAH.

Of the various therapeutic approaches to treat PAH currently available, prostacyclin-based therapies are probably the most potent. It has been shown that $PGI_2$ agonists stimulate ATP release from erythrocytes via a signaling pathway that requires increases in cyclic adenosine monophosphate (cAMP). The erythrocyte-derived ATP is capable of vasodilating isolated-perfused lungs, the cells of which contain $PGI_2$ receptors.

However, prostacyclin-based therapies often result in undesired side effects and delivery issues. Prostacyclin can be inactivated by a low pH, making it unsuitable for oral administration because the low pH in the stomach can inactivate the compound. Furthermore, the half-life of prostacyclin in the blood is 3-5 minutes, which can demand continuous delivery in order to achieve a sustained pharmacologic effect. Prostacyclin agonists address some issues related to undesired side effects and delivery issues, but a need remains to develop new methods for treating PAH, and new methods for screening for effective $PGI_2$ agonists for treating PAH.

SUMMARY OF THE INVENTION

One embodiment of the invention relates a method of treating pulmonary arterial hypertension (PAH) comprising: stimulating ATP release from erythrocytes comprising co-administering to a subject in need thereof an amount of a PDE5 inhibitor compound, or a pharmaceutically acceptable salt, N-oxide, ester, quaternary ammonium salt, hydrate or prodrug thereof, and an amount of a prostacyclin compound, or a pharmaceutically acceptable salt, N-oxide, ester, quaternary ammonium salt, hydrate or prodrug thereof.

Another embodiment of the invention relates a method of screening for therapeutic agents useful for treating pulmonary hypertension comprising: contacting an erythrocyte with a PDE5 inhibitor compound; contacting the erythrocyte with a prostacyclin compound; and detecting a presence or absence of erythrocyte-derived adenosine triphosphate.

Another embodiment of the invention relates a method of screening for a therapeutic agent useful for treating pulmonary hypertension comprising: contacting an erythrocyte with a candidate therapeutic agent; and detecting a presence or absence of erythrocyte-derived adenosine triphosphate, wherein a greater erythrocyte-derived adenosine triphosphate level indicates the candidate therapeutic agent has greater activity in treating pulmonary hypertension.

BRIEF DESCRIPTION OF THE DRAWINGS

FIG. 1 shows identification of the phosphodiesterase 5 (PDE5A) isoform in human erythrocytes.

FIG. 2 shows that the prostacyclin analog UT-15 stimulates increases in ATP release from human erythrocytes and that these increases are potentiated by the PDE5 inhibitor, zapranist.

FIG. 3 demonstrates that at concentration of 10 to 100 nM UT-15 alone does not stimulate ATP release from human erythrocytes. However, at 30 and 100 nM, UT-15 and zapranist (ZAP) induce a response from healthy human erythrocytes.

DETAILED DESCRIPTION OF THE PREFERRED EMBODIMENTS

Unless otherwise specified, "a" or "an" means "one or more".

The phrase "co-administer" as used herein means that the therapeutic agent that inhibits PDE5 and the prostacyclin-based therapeutic agent are administered so that their effective periods of biological activity will overlap in the subject being treated. Co-administration can be carried out by contemporaneous administration of additional therapeutic agents, that is, administering a second medicament before, during, or after the administration of a medicament comprising the compound of the invention.

Method of Screening

Although not wishing to be bound by theory, an aspect of the present invention is thought to disclose an alternative mechanism by which $PGI_2$ agonists and PDE5 inhibitors interact to stimulate pulmonary vasodilatation making erythrocytes novel targets for development of new therapies for PAH. This is thought to occur by a new biologic pathway wherein PDE5 inhibitors can enhance $PGI_2$ agonist-induced ATP release in erythrocytes. Accordingly, some embodiments of the invention relate to screening for a potential therapeutic agent useful for treating PAH.

Accordingly, an embodiment provides a method for screening for therapeutic agents useful for treating pulmonary hypertension comprising: contacting an erythrocyte with a PDE5 inhibitor compound; contacting the erythrocyte with a prostacyclin compound; and detecting a presence or absence of erythrocyte-derived adenosine triphosphate. Typically, the method comprises contacting an erythrocyte with a PDE5 inhibitor in conjunction with, or followed by, or prior to contacting the erythrocyte with a prostacyclin compound and detecting the presence of erythrocyte-derived adenosine triphosphate. The PDE5 inhibitor compound and prostacyclin compound can be selected from the compounds described herein or compounds known in the art as useful in the treatment of PAH.

The effect of contacting an erythrocyte with a PDE5 inhibitor compound and a prostacyclin compound, which may be suitable for use as a therapeutic agent, is an increased presence of erythrocyte-derived adenosine triphosphate. In one embodiment, treatment of the erythrocyte by contacting it with either a PDE5 inhibitor compound or a prostacyclin compound alone will result little or no release of erythrocyte-derived adenosine triphosphate, but treatment of the erythrocyte by contacting it with the same PDE5 inhibitor compound and prostacyclin compound successively or in combination results in an increased release of erythrocyte-derived adenosine triphosphate. In some instances, the release of erythrocyte-derived adenosine triphosphate is increased from an undetectable amount to a detectable amount of erythrocyte-derived adenosine triphosphate. In another embodiment, treatment of the erythrocyte by contacting it with a PDE5 inhibitor compound and a defined concentration of prostacyclin compound successively or in combination results in the presence of erythrocyte-derived adenosine triphosphate, whereas treatment of the same erythrocyte treated with the same defined concentration of prostacyclin compound, but without contacting the erythrocyte with PDE5 inhibitor compound results in a reduced amount of released erythrocyte-derived adenosine triphosphate. In some instances the amount of released erythrocyte-derived adenosine triphosphate is reduced to an undetectable amount.

The erythrocyte can be isolated from a human. More than one erythrocyte can be present, such as for example, a plurality of erythrocytes in the form of a sample of blood or derived from a sample of blood. As used herein, erythrocyte may refer to one, or more than one, erythrocyte.

Either or both of the PDE5 inhibitor compound and the prostacyclin compound can in the form of a solution when contacted with the erythrocyte. The PDE5 inhibitor compound and/or the prostacyclin compound can be present in a solution defined concentration which contains the erythrocyte. The concentration of the prostacyclin compound may be, for example, 1 to 200 nM or 20 to 100 nM. However, concentrations may also be outside of this realm, depending on the ability of the PDE5 inhibitor compound and the prostacyclin compound to induce an increased presence of erythrocyte-derived adenosine triphosphate.

In another embodiment the method of screening for a therapeutic agent useful for treating pulmonary hypertension comprising contacting an erythrocyte with a candidate therapeutic agent; and detecting a presence or absence of erythrocyte-derived adenosine triphosphate, wherein a greater erythrocyte-derived adenosine triphosphate level indicates the candidate therapeutic agent has greater activity in treating pulmonary hypertension.

The candidate therapeutic agent is not particularly limited; however, in some embodiments the candidate therapeutic agent is a PDE5 inhibitor compound and/or a prostacyclin compound, such as for example, the compounds described herein.

Detecting a presence or absence of erythrocyte-derived adenosine triphosphate may be done relative to a baseline measurement. For example, see FIGS. 2 and 3.

In one embodiment the erythrocyte-derived adenosine triphosphate concentration in skeletal muscle and/or isolated lungs is in the micromolar range, such as for example, about 1.0 µM to about 100 µM or about 1.0 µM to about 50 µM or about 1.0 µM to about 10 µM or about 0.1 µM to about 100 µM. In another embodiment, the erythrocyte-derived adenosine triphosphate concentration in skeletal muscle and/or isolated lungs is in the sub-micromolar range, such as for example about 1.0 nM to about 100 nM, or about 1.0 to about 50 nM, or about 1.0 to about 10 nM, or about 10 nM to about 100 nM, or about 10 nM to about 500 nM or about 100 nM to about 500 nM. It is understood that these ranges are not limiting, and other values within the micromolar to sub-micromolar are envisioned.

Method of Treatment

Because the present invention is thought to demonstrate an alternative mechanism by which $PGI_2$ agonists and PDE5 inhibitors interact to stimulate pulmonary vasodilatation, several embodiments of this invention contemplate methods in which erythrocytes are novel targets for development of new therapies for PAH.

Accordingly, in one embodiment the invention provides a method of treating PAH by stimulating ATP release from erythrocytes through co-administration to a subject in need thereof an amount of a PDE5 inhibitor compound, and an amount of a prostacyclin compound. The compounds may be administered as a sole therapy or in combination with other treatments. Co-administration can be carried out by contemporaneous administration of additional therapeutic agents.

The compounds may be administered as pharmaceutical compositions selected with regard to the intended route of administration and standard pharmaceutical practice. Such pharmaceutical forms may take a form suitable for oral, pulmonary or parenteral administration and may be prepared by conventional manner using conventional excipients. For example, for parenteral injection (including intravenous, subcutaneous, intramuscular, intravascular or infusion) the composition may take the form of, for example, a sterile solution, suspension or emulsion.

Methods of delivering prostacyclin compounds and PDE5 compounds in a manner effective for causing a pharmacological effect for PAH are well documented in the art, and would be readily apparent to one skilled in the art.

In some embodiments, the present invention comprises a method of treating pulmonary arterial hypertension (PAH) comprising stimulating ATP release from erythrocytes comprising co-administering to a subject in need thereof an amount of a PDE5 inhibitor compound, or a pharmaceutically acceptable salt, N-oxide, ester, quaternary ammonium salt, or prodrug thereof, and an amount of a prostacyclin compound, or a pharmaceutically acceptable salt, N-oxide, ester, quaternary ammonium salt, or prodrug thereof. Additionally, the co-administration of the amount of PDE5 inhibitor and the amount of prostacyclin compound may, in an embodiment, stimulate an increased ATP release from erythrocytes as compared to administration of a same amount of the prostacyclin compound without co-administration of a PDE5 inhibitor. In another astpect, the method provides for the administration of the amount of the prostacyclin compound is such that administration of the amount of the prostacyclin compound without administration of the amount of PDE5 inhibitor does not stimulate ATP release from erythrocytes.

Prostacyclin Compounds

The prostacyclin compound used in the methods disclosed herein can be any type of prostacyclin ($PGI_2$), or an analogue or agonist thereof, known in the art, such as any prostacyclin compound in the eicosanoid family. In one embodiment, the prostacyclin compound can be any prostacyclin ($PGI_2$) and/or its analogue suitable to treat symptoms of PAH when co-administered with a PDE5 inhibitor compound. Additionally, the prostacyclin compound can be any prostacyclin ($PGI_2$) and/or an analogue recognized in the art as resulting in clinical benefit in PAH. For example, the prostacyclin analogue can be epoprostenol, treprostinil, iloprost, beraprost, an analogue of any thereof, combinations thereof, or pharmaceutically acceptable salt, N-oxide, ester, quaternary ammonium salt, hydrate or prodrug thereof. In an embodiment, the prostacyclin compound is a prostaglandin derivative, such as for example, a benzidene prostaglandin. In one embodiment, the benzidene prostaglandin is selected from those disclosed in U.S. Pat. Nos. 5,153,222, 7,417,070, 7,544,713, 6,521,212 and 6,756,033, which are all incorporated by reference in their entirety. In one embodiment, the prostacyclin analogue is the benzidene prostaglandin UT-15, which is treprostinil or pharmaceutically acceptable salt, N-oxide, ester, quaternary ammonium salt, hydrate or prodrug thereof.

Phosphodiesterase Type-5

The phosphodiesterase inhibitor used in the methods disclosed herein can be any type of phosphodiesterase type-5 inhibitor (PDE5), or an analogue that is known in the art. It is recognized herein that the methods of screening disclosed herein may reveal clinically useful PDE5 compounds that were previously believed to be ineffective for PAH. By way of non-limiting example, some PDE5 compounds that are contemplated for use in the embodied methods are selected from the group consisting of sildenafil, tadalafil, vardenafil, avanafil, zaprinast, dipyridamole, 3-isobutyl-1-methylxanthine (IBMX), propentofylline, papaverine, 4-bromo-5-(pryidylmethylamino)-6-[3-(4-chlorophenyl)propxy]-3(2H)pyridazinone, 1-[4-[(1,3-benzodiozol-5-9pyridylmethylamino)-6-chloro-2-quinazolinyl]-4-piperidine-carboxylic acid, (+)-cis-5,6a,7,9,9,9a-hexahydro-2-[4-(trifloromethyl)-phenylmethyl-5-methyl cyclopent-4,5]imidazo[2.1-b]purin-4(3H)one, furazlocillin, cis-2-hexyl-5-methyl3,4,5,6a,7,8,9, 9a-octahydrocyclopent[4,5]imidazo[2,1-b]purin-4-one, 3-acetyl-1-(2-chlorobenzyl)-2-propylindole-6-carboxylate, 4-bromo-5-(3-pyridylmethylamino)-6-(3-(4-chlorophenyl) propoxy)-3(2H)pyridazinone, 1-methyl-5-(5morpholinoacetyl-2-n-propoxyphenyl)-3-n-propyl-1,6-dihydro-7H-pyrazolo(4,3-d)pyrimidin-7-one, 1-[4[(1,3-benzyodioxol-5-methyl)amino]-6-chloro-2-quinazolinyl]4-piperidine carboxylic acid, an analogue of any thereof, combinations thereof, or pharmaceutically acceptable salt, N-oxide, ester, quaternary ammonium salt, hydrate or prodrug thereof.

The present invention, thus generally described, will be understood more readily by reference to the following examples, which are provided by way of illustration and are not intended to be limiting of the present invention.

NON-LIMITING WORKING EXAMPLES

Erythrocyte ATP release was measured in both the absence and presence of (a) the $PGI_2$ agonist, treprostinil in the form of UT-15 or its vehicle, saline, and (b) alone or in combination with the selective PDE5 inhibitor, zapranist (ZAP, 10 μM). Erythrocytes treated with UT-15 (1 uM, n=7) demonstrated an increase in ATP release compared to controls that was potentiated by ZAP pretreatment (P<0.05). When erythrocytes were incubated with UT-15 at 30 nM (n=7) or 100 nM (n=7), no ATP release was detected. However, when the same cells were pretreated with ZAP, ATP release was stimulated by both concentrations (30 nM (n=7) or 100 nM (n=7)) of UT-15, a seen in FIG. 3.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. A method of treating pulmonary arterial hypertension (PAH) and stimulating ATP release from erythrocytes comprising:
co-administering to a subject in need thereof an amount of a PDE5 inhibitor compound, or a pharmaceutically acceptable salt thereof, and an amount of a prostacyclin compound, or a pharmaceutically acceptable salt thereof, wherein said co-administering stimulates ATP release from erythrocytes of the subject, wherein the PDE5 inhibitor compound, or the pharmaceutically acceptable salt thereof, is selected from the group consisting of tadalafil, zaprinast, pharmaceutically acceptable salts thereof, and combinations thereof and wherein the prostacyclin compound, or the pharmaceutically acceptable salt thereof, is treprostinil, or a pharmaceutically acceptable salt thereof.

2. The method of claim 1 wherein the co-administration of the amount of the PDE5 inhibitor, or the pharmaceutically acceptable salt thereof, and the amount of the prostacyclin compound, or the pharmaceutically acceptable salt thereof, stimulates an increased ATP release from erythrocytes as compared to administration of a same amount of the prostacyclin compound, or the pharmaceutically acceptable salt thereof, without co-administration of the PDE5 inhibitor, or the pharmaceutically acceptable salt thereof.

3. The method of claim 1, wherein administration of the amount of the prostacyclin compound, or the pharmaceutically acceptable salt thereof, is such that administration of the amount of the prostacyclin compound, or the pharmaceutically acceptable salt thereof, without administration of the amount of the PDE5 inhibitor, or the pharmaceutically acceptable salt thereof, does not stimulate ATP release from erythrocytes.

4. The method of claim 1, wherein the prostacyclin compound, or the pharmaceutically acceptable salt thereof, is a pharmaceutically acceptable salt of treprostinil.

5. The method of claim 1, wherein the PDE5 inhibitor compound, or the pharmaceutically acceptable salt thereof, is zaprinast, or a pharmaceutically acceptable salt thereof.

6. The method of claim 1, wherein the subject in need thereof is a human.

7. The method of claim 1, wherein the PDE5 inhibitor compound, or the pharmaceutically acceptable salt thereof, is tadalafil, or a pharmaceutically acceptable salt thereof.

* * * * *